United States Patent [19]

Phillips et al.

[11] Patent Number: 4,816,264

[45] Date of Patent: Mar. 28, 1989

[54] SUSTAINED RELEASE FORMULATIONS

[75] Inventors: Reginald Phillips, Montclair; Krishnayya Bikkina, Edison; Sadath U. Khan, Mine Hill, all of N.J.

[73] Assignee: Warner-Lambert Company, Morris Plains, N.J.

[21] Appl. No.: 871,643

[22] Filed: Jun. 6, 1986

[51] Int. Cl.$^4$ .................. A61K 9/22; A61K 9/36; A61K 9/16

[52] U.S. Cl. .................. 424/468; 424/480; 424/482; 424/494; 424/495; 424/497; 427/3

[58] Field of Search ............... 424/472, 468, 480, 482, 424/494, 495, 497; 427/3

[56] References Cited

U.S. PATENT DOCUMENTS

| | | | |
|---|---|---|---|
| 4,008,719 | 2/1977 | Theeuwes et al. | 128/260 |
| 4,014,334 | 3/1977 | Theeuwes et al. | 128/260 |
| 4,252,786 | 2/1981 | Weiss et al. | 424/19 |
| 4,309,996 | 1/1982 | Theeuwes | 128/260 |
| 4,320,759 | 3/1982 | Theeuwes | 128/260 |
| 4,389,393 | 6/1983 | Schor et al. | 424/19 |
| 4,434,153 | 2/1984 | Urquhart et al. | 424/22 |
| 4,519,801 | 5/1985 | Edgren | 604/892 |
| 4,610,870 | 9/1986 | Jain et al. | 424/19 |

FOREIGN PATENT DOCUMENTS 1568837  6/1980  United Kingdom .

OTHER PUBLICATIONS

"Coating of Tablets and Small Particles with Acrylic Resins by Fluid Bed Technology", K. Lehmann & D. Dreher, Int. J. Pharm. Tech. & Prod. Mfr., 2 (4) 31-43, (1981).

"The Application and Processing of Acrylic Coatings in Form of Aqueous Dispersions Compared with Organic Solutions" Klaus Lehmann, Eripainos:Acta Pharmaceutica Fennica, No. 4/1982.

*Primary Examiner*—Michael Lusignan
*Attorney, Agent, or Firm*—Howard Olevsky; Ronald A. Daignault

[57] ABSTRACT

Drug delivery systems which exhibit sustained release properties when administered are produced using a "dual control" system which employs polymeric agents in core and membrane portions.

7 Claims, No Drawings

SUSTAINED RELEASE FORMULATIONS

BACKGROUND

The self-administration of oral dosage forms is fought with many non-compliance problems. While some patients do not like the taste or mouthfeel of certain dosage forms, others simply forget to take drugs or other orally-administered beneficial substances.

This invention deals with a dosage form which need be taken no more than twice in a twenty-four hour period. Optimally it need be administered only once a day.

THE INVENTION

It has been discovered that certain binders and coating systems, when used together, result in a "dual control" mechanism which prolongs the release of drugs and other beneficial substances for up to 12 hours and more.

In one preferred embodiment, procainamide hydrochloride is mixed with a hydrocolloid gelling polymer such as hydroxyethyl cellulose, and conventional additives such as sugar and fillers, and shaped into a core. This core is then coated with a semipermeable membrane containing a mixture of a hydroxypropyl cellulose polymer, Eudragit E30D (a 30% dispersion of methacrylate ester copolymer in aqueous media), conventional coating additives such as an antifoam agent, polyethylene glycol, and filler.

The core alone gives drug release in 8 to 9 hours. The core/membrane combination gives sustained release properties over a period of 12 hours or more.

In another embodiment, the coated sustained release product described above is further coated with a color coat and a clear coat.

ADVANTAGES

The invention has several advantages over other dosage forms. Primarily, it helps to assure patient compliance in the self-administration or oral dosages because only 1 or 2 dosages need be taken per day.

Secondly, the "dual" nature of the system virtually eliminates the likelihood that the drug or other bioaffecting agent will be "dumped" into the recipient's system soon after swallowing. The invention is of particular benefit in the administration of antiarrythmics, antihypertussives and other drugs whose sustained action is important to their efficacy.

Other aspects and advantages of the invention will become apparent from the following description.

DESCRIPTION OF THE INVENTION

The heart of the invention is a delivery system for drugs or other beneficial agents. While the term "drug" is used, it should be noted that the invention is equally applicable to vitamins, minerals, and other beneficial agents to be discussed in greater detail infra. The delivery system of the invention contains two parts:

(1) A tablet core produced by mixing drug and a gelling polymer shaping and hardening, pre drying, and (2) A semipermeable membrane or coating which surrounds the core.

It is the combination of a polymer-bound core and a polymeric membrane outside the core which results in the flow release of the active component(s) from the case of the delivery system. The resultant composite is then useful as an ingestible tablet or pellet.

THE CORE

The core portion of the novel dosage system contains at least one beneficial substance or drug and at least one gelling polymer.

By "beneficial substance," applicants mean any agent or combination of agents which, when absorbed by the body, evokes a response which mitigates against one or more disease states or symptoms or otherwise improves the health of the individual to whom it was administered. In general, any drug, pro-drug, vitamin, mineral or functionally equivalent substance can be used.

The drugs or other beneficial substances used herein may be selected from a wide variety of molecules and their acid addition salts. Both organic and inorganic salts may be used provided the drug maintains its medicament value and is soluble in the solvent. Exemplary acid salts include hydrochloride, hydrobromide, orthophosphate, benzoate, maleate, tartrate, succinate, citrate, salicylate, sulfate, and acetate.

Suitable categories of drugs that may be employed in the instant composite may vary widely and generally may include any stable drug combination. Illustrative categories and specific examples include:

(a) Antitussives, such as dextromethorphan, dextromethorphan hydrobromide, noscapine, carbetapentane citrate, and chlophedianol hydrochloride;

(b) Antihistamines, such as chlorpheniramine maleate, phenindamine tartrate, pyrilamine maleate, doxylamine succinate, and phenyltoloxamine citrate, (c) Decongestants, such as phenyleprine hydrochloride, phenylpropanolamine hydrochloride, pseudophedrine, hydrochloride ephedrine; and (d) Various alkaloids, such as codeine phosphate, codeine sulfate and morphine.

(e) Antihypertensives (f) Antiarythmics (g) Antiinflammation agents (h) Antibacterials (i) Vitamins (j) Mineral supplements, such as potassium chloride and calcium carbonates and the like. Mixtures are operable.

Useful drugs include, but are not limited to: procainamide, hydrochloride, meclofenamic acid, gemfibrozil, diphenhydramine, diphenhydramine HCl, and the like.

Mixtures of beneficial substances can be employed.

The gelling polymers used to bind the drug in the core portion are generally polymer materials which form gels or colloids. It is believed that this polymeric ingredient yields a gel within or adjacent to the core when it comes in contact with an aqueous media such as that inside a subject who ingests the dosage form.

Useful gelling polymers are those bearing molecular weight of about 270,000 to about 1,150,00, preferably about 860,000 to about 1,150,000. Furthermore, these polymers should have an intrinsic viscosity of from about 90 to about 4,000 cps, preferably about 1500, to 4000 cps, in about 1% aqueous solution.

Typically, these polymers are cellulosics, although a portion or all of any cellulosic gelling polymer can be replaced with one or more of such polymers as polyvinyl acetate phthalate, polyvinyl pyrollidone, polyethylene oxide and the like.

Useful cellulosics include ethers, esters and gums. Thus, hydroxy ethyl cellulose (types H, HH, H4, MH, M,L) hydroxypropyl cellulose (typexs HF, EF, LF, MF), hydroxy propyl methylcellulose (types E4M, F4M, K4M, K15M, E15LV, XD), cellulose acetate phthalate, carboxymethyl cellulose, sodium carboxymethyl cellulose, and the like. Mixtures are operable.

The key feature of the gelling polymer is its solubility and its propensity to form a membrane in aqueous environments.

The core or central portion can also contain conventional excipients and additives which function to facilitate in processing and/or storage. Thus, colorants, colorants, flavors, perfumes, sweeteners, surfactants, lubricants, stabilizers and the like, as well as mixtures of two or more of these, can be employed.

Typically, the structure employed will comprise sugar. Some or all of the sugar may be replaced by at least one sugar substitute, e.g., aspartame, saccharin, or the like.

Fillers, when present, will be pharmaceutically acceptable. Various conventional additions, e.g. sugar, silica dioxide, magnesium stearate, and the like can be used herein. Thus, silicas of various kinds, e.g., colloidal silica and/or Cab-O-Sil are operable.

One or more lubricants, wetting agents, etc. can also be employed.

Magnesium stearate is one preferred component of the substrate part of the composite delivery system.

In the core portion, the drug content will be about 70 to about 90 wt %, preferably 76.9 to 83.3%.

SEMIPERMEABLE MEMBRANE

The outer shell or membrane adjacent to the central core of the instant delivery system contains a combination of at least two polymeric coating materials.

The first of such materials may be one of the gelling polymers employed in the core of the system. Thus, the cellulosics and other vinyl polymers discussed above are operable. Cellulosics are preferred. Hydroxypropyl cellulose is highly preferred.

The second polymeric material used in the semipermeable membrane is an aqueous dispersion resin of acrylic character. Preferred resins are the Eudragits® made by Rohm Pharma and the Aquacoats® made by FMC Corporation. Eudragit E30D® is highly preferred.

The membrane or outer coating layer may also contain a variety of convention excipients. Thus, antifoam agents, fillers, lubricants, colorants, surfactants, stabilizers, plasticizers, sweeteners, flavoring agents and the like and mixtures thereof may be employed.

Useful additions of this include Antifoam AF® made by Dow Chemical Co. polyethylene glycol 3550, Mistron® talc from Whittaker and the like.

The exterior or outer membrane can be the final coating applied to the dosage form. However, the use of one or more additional coating layers such as color coats, polishing coats, clear coats and other conventionally used coats is contemplated.

The final dosage form will be a solid orally-administrable form. While tablets or pills are preferred, the delivery system may comprise pellets, caplets and the like of oval, elliptical, spherical or other conventional shapes.

The final composition of the dosage form will be such that it will contain about 65 to about 80, preferably about 70.9 to about 77.0 weight percent drug, about 20 to about 30, preferably about 22.4 to about 28.6, binder component (including gelling and membranal polymeric binders) and about 2 to about 3 weight percent excipient(s).

Generally, the total film coat per tablet, in a tablet embodiment, will be from about 5 to about 10 wt %, preferably about 5 to about 6 wt %.

EXAMPLES

The following examples illustrate the invention:

EXAMPLES 1-3

Table I sets forth three preferred embodiments of compositions for tablet cores and film coatings produced in accordance with the invention.

TABLE I

| Tablet Cores | | | |
|---|---|---|---|
| | Dose | | |
| | 500 mg | 750 mg | 1000 mg |
| Procanamide Hydrochloride USP | 76.90% | 83.30% | 83.30% |
| Hydroxethyl Cellulose NF Type 250 H NF | 2.60% | 1.70% | 1.70% |
| Purified Water USP | q.s. | q.s. | q.s. |
| Silicon Dioxide, Colloidal NF | 0.20% | 0.20% | 0.20% |
| Magnesium Stearate, NF | 0.30% | 0.40% | 0.40% |
| Film Coat Composition | | | |
| Hydroxypropyl Cellulose NG | 3.00% | 3.00% | 3.00% |
| Antifoam | 0.30% | 0.30% | 0.30% |
| Polyethylene Glycol 3350 NF | 0.60% | 0.70% | 0.70% |
| Eudragit E30D | 25.00% | 20.00% | 20.00% |
| Talc | 8.00% | 6.00% | 6.00% |
| Purified Water | 63.10% | 70.00% | 70.00% |
| Total Film Coat Per Tablet | 5.50% w/w | 6.00% w/w | 5.50% w/w |

EXAMPLE 4

This example illustrates the preparation of 500 mg procainamide hydrochloride tablets.

500.00 grams procainamide hydrochloride was passed through a Fitzmill #N00RH screen with impact at highspeed. The powder was loaded into a planetary mixer 130 grams hydroxy ethyl cellulose, type "H" was added and the powder was blended for 5 minutes to a loose density of 0.36g/ml.

A solution was made up using 17.00g or g.s. sugar and 20.00 ml or q.s. purified water. The blended powder mixture was granulated using this solution and additional water as needed. Core was taken not to over overwet the granulate.

The granulate was spread on paper-lined trays and dried overnight in forced air ovens at 50-55° C. to a L.O.D. of about 0.6 (±0.3%).

The dried material was mixed with 1.00 g. colloidal silica, and 2.00g. magnesium stearate and passed through a Fitzmill #2A RH screen with knives at medium speed to give a final granulation have a loose density of 0.58 g/ml. This granulate was then tumble blended for 5 minutes in a P-K blender. 650 mg of the blended product was compressed in using 0.375"×0.630" elliptical punches to yield elliptical tablets having 12-15 kp hardness and 0.290-0.294" thickness.

The coating of the cores produced above was carried out as follows:

A. Semipermeable membrane subcoat

The basic recipe calls for the use of 250 g. of solution to coat 1 kg. of tablets.

6.3 g of antifoam AF Emulsion was mixed well with 1325.1 g purified water. 12.6 g of polyethylene glycol 3350 was added and mixing continued until the PEG dissolved. 63.0 g. of hydroxypropyl cellulose was dispersed into the mixture and was allowed to hydrate with mixing for 30 minutes. 525.0 g. Eudragit E 30D was added and mixing continued at moderate speed. 168.0 g. of Mistron spray talc was added with continued mixing throughout the coating process. The subcoat, as first coat(ing) is then in place.

B. Color Coat

About 150 g. of color coating solution is needed to coat 1 kg of tablets. 2.52 g. antifoam emulsion and 1068.48 g. purified water was mixed to create a vortex. 189 g. Opadry yellow colorant was added slowly and mixed for 30 minutes.

C. Clear Coat

About 65 g. of clear coating solution is needed to coat 1 kg. of tablets. 0.1638 g. vanillin and 10.92 g. polyethylene glycol 3350 were dissolved in 507.62 g. purified water. 27.3 g. hydroxy ethyl cellulose was added and mixed until it dissolved.

APPLICATION OF COATINGS

Typically, the coating are applied to cores in quantities of about 5 to 6 wt. % sub-coat, followed by about 2 to 2.5 wt. % color coat and about 0.5 wt. % clear coat using a 24" Accela Cota pan and the following parameters:

|  | SUB-COAT | COLOR COAT | CLEAR COAT |
|---|---|---|---|
| Pan Load (kg) | 6 to 8 | 6 to 8 | 6 to 8 |
| Pan Speed (rpm) | 14 | 14 | 14 |
| Inlet Air Temp. (°C.) | 60–80 | 60–80 | 60–80 |
| Tablet Bed Temp. (°C.) | 36–38 | 37–39 | 37–39 |
| Fluid Nozzle | L3B | L3B | L3B |
| Air Nozzle | 66 PD | 66 PD | 66 PD |
| Atomizing Pressure (psi) | 40 | 40 | 40 |
| Cylinder Pressure (psi) | 50 | 50 | 50 |
| Spray Rate (ml/min) | 25–40 | 20–30 | 20–30 |

The resultant tablets were ellipitical in shape, had a vanillin odor and a yellow color.

EXAMPLE 5

Using similar procedures to those and in Example 4 tablets were made using the following compositions.

| Tablet Core Compositions (1000 tablets) | |
|---|---|
| Procainamide Hydrochloride USP | 750.00 g |
| Hydroxyethyl Cellulose NF, Type "H" q.s. or | 130.00 g |
| Sugar, Granulated NF Special (Bottler's Grade) | 15.00 g |
| Purified Water USP q.s. or | 30.00 ml |
| Silicon dioxide, Colloidal NF/Cab-O-Sil M-5 | 2.00 g |
| Magnesium Stearate, NF - Mallinkrodt q.s. or | 3.00 g |
|  | 900.00 g |

| TABLET COATING COMPOSITIONS | | |
|---|---|---|
| A. Sub-Coat | | |
| Hydroxypropyl Cellulose NF | 3.0 | q.s. |
| Antifoam AF Emulsion, Medical | 0.3 | q.s. |
| Polyethylene Glycol 3350 NF | 0.7 | q.s. |
| Eudragit E30D | 20.00 | q.s. |
| Mistron Spray Talc | 6.00 | q.s. |
| Purified Water USP | 70.00 | q.s. |
| To Make About: | 954.00 g | |
| B. Color Coat: | | |
| Opadry Orange YS-1-2563 | 15.00 | q.s. |
| Antifoam AF Emulsion, Medical | 0.20 | q.s. |
| Purified Water USP | 84.80 | q.s. |
| To Make About | 973.10 g | |
| C. Clear Coat: | | |
| Vanillin USP | 0.03 | q.s. |
| Hydroxyethyl Cellulose NF, Type L | 5.00 | q.s. |
| Polyethylene Glycol 3350 NF | 2.00 | q.s. |
| Purified Water USP | 92.97 | q.s. |
| To Make About | 978.00 g | |

EXAMPLE 6

Using procedures similar to those used in Example 4, one thousand tablets were made using the following compositions:

| Tablet Cores: | |
|---|---|
| Procainamide Hydrochloride USP | 1000.00 g |
| Hydroxyethyl Cellulose NF, Type "H" q.s. or | 173.30 g |
| Sugar, Granulated NF, Special (Bottler's grade) | 20.00 g |
| Purified Water USP q.s. or q.s. or | 40.00 ml |
| Silicon dioxide, Colloidal NF/Cab-O-Sil M-5 q.s. | 2.70 g |
| Magnesium Stearate, NF - Mallinkrodt q.s. or | 4.00 g |
| To Make: | 1200.00 g |

| TABLET FILM COATINGS: | | |
|---|---|---|
|  | Wt. % | |
| A. Sub-Coat: | | |
| Hydroxypropyl Cellulose NF | 3.0 | q.s. |
| Antifoam AF Emulsion, Medical | 0.3 | q.s. |
| Polyethylene Glycol 3350 NF | 0.7 | q.s. |
| Eudragit E30D | 20.0 | q.s. |
| Mistron Spray Talc | 6.0 | q.s. |
| Purified Water USP | 70.0 | q.s. |
| To Make About: | 1266.00 g | |
| B. Color Coat: | | |
| Opadry Red/Orange YS-1-2435 | 15.0 | q.s. |
| Antifoam AF Emulsion, Medical | 0.2 | q.s. |
| Purified Water USP | 84.8 | q.s. |
| To Make About: | 1291.50 g | |
| C. Clear Coat: | | |
| Vanillin USP | 0.03 | q.s. |
| Hydroxyethyl Cellulose NF, Type L | 5.00 | q.s. |
| Polyethylene Glycol 3350 NF | 2.00 | q.s. |
| Purified Water USP | 92.97 | q.s. |
| To Make About: | 1298.00 g | |

EXAMPLE 7

Using procedures similar to those used in Example 4, one thousand tablets were made using the following compositions:

| TABLET CORES: | |
|---|---|
| Procainamide Hydrochloride USP | 500.00 g |
| Hydroxyethyl Cellulose NF, Type "H" q.s. or | 130.00 g |
| Sugar, Fine granulated NF q.s. or | 17.00 g |
| Purified Water USP q.s. or | 20.00 ml |
| Silicon dioxide, Colloidal NF/Cab-O-Sil M-5 q.s. | 1.00 g |
| Magnesium Stearate, NF - Mallinkrodt q.s. or | 2.00 g |
|  | 650.00 g |

| TABLET FILM COATING: | |
|---|---|
| Wt % | |
| A. Sub-Coat: | |

-continued

TABLET FILM COATING:

| | Wt % | |
|---|---|---|
| Hydroxypropyl Cellulose NF | 3.00% | q.s. |
| Antifoam AF Emulsion, Medical | 0.30% | q.s. |
| Polyethylene Glycol 3350 NF | 0.60% | q.s. |
| Eudragit E3OD | 25.00% | q.s. |
| Mistron Spray Talc | 8.00% | q.s. |
| Purified Water USP | 63.10% | q.s. |
| To Make About: | | 685.80 g |

B. Color Coat:

| | | |
|---|---|---|
| Opadry Yellow YS-1-2165 | 15.00% | q.s. |
| Antifoam AF Emulsion, Medical | 0.20% | q.s. |
| Purified Water USP | 84.80% | q.s. |
| To Make About: | | 702.00 g |

C. Clear Coat:

| | | |
|---|---|---|
| Vanillin USP | 0.03% | q.s. |
| Hydroxyethyl Cellulose NF, Type L | 5.00% | q.s. |
| Polyethylene Glycol 3350 NF | 2.00% | q.s. |
| Purified Water USP | 92.97% | q.s. |
| To Make About: | | 705.30 g |

EXAMPLE 8

Dissolution tests were run on the tablets made in accordance with Examples 6 and 7.

The procedure for the study was USP Method II (Paddles at 50 rpm) first in 0.1NHCl and remaining time in 0.05M. Phosphate buffer at 37° C.

The results of the study are given in Table II.

TABLE II

| | PERCENT DISSOLVED | |
|---|---|---|
| TIME Hours | Comparison of Ex. 7 (500 mg. tablet) | Comparsion of Ex. 6 (1.0 gram tablet) |
| 1 | 3.6 | 2.0 |
| 2 | 13.2 | 9.7 |
| 3 | 24.0 | 18.7 |
| 4 | 34.2 | 27.1 |
| 5 | 43.5 | 35.1 |
| 6 | 52.4 | 42.7 |
| 7 | 60.0 | 49.9 |
| 8 | 66.8 | 56.5 |
| 9 | 72.7 | 62.5 |
| 10 | 78.0 | 68.1 |
| 11 | 82.0 | 73.3 |
| 12 | 86.0 | 77.8 |

While the nature of the final coatings (i.e. color and clear coat(s), when used), is not critical, it is generally preferred that they contain the same types of binders and excipients used in the core and semipermeable membrane compositions.

Reasonable variations, such as those which would occur to a skilled artisan, can be made herein without departing from the scope of the invention.

We claim:

1. In combination, a drug suitable for oral delivery and a delivery system for sustained release dosage of said drug comprising:
   (a) a core portion containing about 70 to 90% by weight of the drug and an effective amount of a cellulosic gelling polymer; and
   (b) a semipermeable membrane around said core containing effective amounts of a water soluble cellulosic polymer and a water insoluble acrylic polymer; said combination having 65 to 80% by weight drug and 20 to 30% by weight of the combination of gelling and membranal polymeric binders of the combination.

2. The delivery system of claim 1 whenever the core contains hydroxyethyl cellulose.

3. The delivery system of claim 2 wherein the drug is procainamide hydrochloride.

4. A process for producing solid dosage forms which exhibit sustained release properties when administered which comprises the steps of:
   (1) producing a solid core containing effective amounts of at least one drug and at least one cellulosic gelling polymer, and
   (2) coating the core of step (1) with at least one semipermeable coating which contains effective amounts of water soluble cellulosic and water insoluble acrylic polymer components.

5. The process of claim 4 wherein the gelling polymer comprises hydroxy ethyl cellulose.

6. The process of claim 4 wherein there is added the steps of:
   (3) coating the product of step (2) with a polymeric color coat, and
   (4) coating the product of step (3) with a polymeric clear coat.

7. The process of claim 6 wherein the gelling polymer comprises hydroxyethyl cellulose.

* * * * *